US008541554B2

(12) United States Patent
Grenier et al.

(10) Patent No.: US 8,541,554 B2
(45) Date of Patent: Sep. 24, 2013

(54) IMMUNOSUPPRESSANT DRUG EXTRACTION REAGENT FOR IMMUNOASSAYS

(75) Inventors: Frank C. Grenier, Libertyville, IL (US); Ryan F. Workman, Gurnee, IL (US); Hina Syed, Gurnee, IL (US); Salman Ali, Hoffman Estates, IL (US)

(73) Assignee: Abbott Laboratories, Abbott Park, IL (US)

(*) Notice: Subject to any disclaimer, the term of this patent is extended or adjusted under 35 U.S.C. 154(b) by 73 days.

(21) Appl. No.: 12/980,877

(22) Filed: Dec. 29, 2010

(65) Prior Publication Data

US 2011/0091997 A1    Apr. 21, 2011

Related U.S. Application Data

(62) Division of application No. 11/490,624, filed on Jul. 21, 2006, now Pat. No. 7,883,855.

(51) Int. Cl.
*C07K 16/00* (2006.01)
*G01N 33/24* (2006.01)

(52) U.S. Cl.
USPC ............ 530/389.8; 435/80; 435/81; 530/421

(58) Field of Classification Search
None
See application file for complete search history.

(56) References Cited

U.S. PATENT DOCUMENTS

| | | | |
|---|---|---|---|
| 4,443,637 A * | 4/1984 | Hillman ........................ 568/876 |
| 4,652,517 A | 3/1987 | Scholl et al. | |
| 4,886,671 A * | 12/1989 | Cryer ............................ 424/641 |
| 5,023,262 A | 6/1991 | Caufield et al. | |
| 5,120,725 A | 6/1992 | Kao et al. | |
| 5,120,727 A | 6/1992 | Kao et al. | |
| 5,120,842 A | 6/1992 | Failli et al. | |
| 5,135,875 A | 8/1992 | Meucci et al. | |
| 5,169,773 A | 12/1992 | Rosenthaler et al. | |
| 5,177,203 A | 1/1993 | Failli et al. | |
| 5,217,971 A | 6/1993 | Takasugi et al. | |
| 5,260,048 A * | 11/1993 | Ryan ............................ 435/40.5 |
| 5,322,772 A | 6/1994 | Soldin | |
| 5,338,684 A | 8/1994 | Grenier et al. | |
| 5,350,574 A | 9/1994 | Erlanger et al. | |
| 5,354,845 A | 10/1994 | Soldin | |
| 5,489,668 A | 2/1996 | Morrison | |
| 5,498,597 A | 3/1996 | Burakoff et al. | |
| 5,525,523 A | 6/1996 | Soldin | |
| 5,650,228 A | 7/1997 | May | |
| 5,650,288 A | 7/1997 | MacFarlane et al. | |
| 5,698,448 A | 12/1997 | Soldin | |
| 5,750,413 A | 5/1998 | Morrison et al. | |
| 5,780,307 A | 7/1998 | Soldin | |
| 5,897,990 A | 4/1999 | Baumann et al. | |
| 5,955,108 A | 9/1999 | Sutton et al. | |
| 5,990,150 A | 11/1999 | Matsui et al. | |
| 6,054,303 A | 4/2000 | Davalian et al. | |
| 6,187,547 B1 | 2/2001 | Legay et al. | |
| 6,197,588 B1 | 3/2001 | Gray et al. | |
| 6,239,102 B1 | 5/2001 | Tiemessen | |
| 6,328,970 B1 | 12/2001 | Molnar-Kimber et al. | |
| 6,410,340 B1 | 6/2002 | Soldin | |
| 6,541,612 B2 | 4/2003 | Molnar-Kimber et al. | |
| 6,913,580 B2 | 7/2005 | Stone | |
| 6,998,246 B2 | 2/2006 | Schäffler et al. | |
| 7,189,582 B2 | 3/2007 | Chen et al. | |
| 2002/0002273 A1 | 1/2002 | Sedrani et al. | |
| 2002/0022717 A1 | 2/2002 | Sedrani et al. | |
| 2002/0055124 A1 | 5/2002 | Janda et al. | |
| 2002/0055126 A1 | 5/2002 | Schaffler et al. | |
| 2002/0151088 A1 | 10/2002 | Molnar-Kimber et al. | |
| 2003/0157556 A1 | 8/2003 | Maggiore et al. | |
| 2003/0235839 A1 | 12/2003 | McKernan et al. | |
| 2004/0062793 A1 | 4/2004 | Dyke | |
| 2004/0101429 A1 | 5/2004 | Ogawa | |
| 2004/0102429 A1 | 5/2004 | Modak | |
| 2005/0033035 A1 | 2/2005 | Beisel et al. | |
| 2005/0112778 A1 | 5/2005 | Wang et al. | |
| 2005/0164323 A1 | 7/2005 | Chaudhary et al. | |
| 2005/0272109 A1 | 12/2005 | Schaffler et al. | |
| 2006/0003390 A1 | 1/2006 | Schaffler et al. | |
| 2006/0062793 A1 | 3/2006 | Webb et al. | |

(Continued)

FOREIGN PATENT DOCUMENTS

| CN | 1331603 | 1/2002 |
|---|---|---|
| CN | 1414971 | 4/2003 |

(Continued)

OTHER PUBLICATIONS

Kohashi et al. Fluorescence reaction of bilirubin with zinc ion in dimethyl sulfoxide and its application to assay of total bilirubin in serum. Analytica Chimica Acta 1998, vol. 365, pp. 177-182.*
Adamczyk, et al., "Chemiluminecent N-Sulfoonyalcridinium-9-Carboxamides and Their Application in Clinical Assays," Luminescence biotechnology: Instruments and Applications, 2002, 77-105.
Alak A.M., "Measurement of Tacrolimus (Fk506) and its Metabolites: A Review of Assay Development and Application in Therapeutic Drug Monitoring and Pharmacokinetic Studies," Therapeutic Drug Monitoring, 1997, vol. 19 (3), pp. 338-351.
Bose B., et al., "Characterization and Molecular Modeling of a Highly Stable Anti-Hepatitis B Surface Antigen scFv," Molecular Immunology, 2003, vol. 40 (9), pp. 617-631.
Brown, et al., "Low Hematocrit and Serum Albumin Concentrations Underlie the Overestimation of Tacrolimus Concentrations by Microparticle Enzyme Immunoassay Versus Liquid Chromatography-Tandem Mass Spectrometry," Clinical Chemistry, 2005, vol. 51 (3), pp. 586-592.
Hatfield R.M., et al., "Development of an Enzyme-Linked Immunosorbent Assay for the Detection of Humoral Antibody to Pasteurella Anatipestifer," Avian Pathology, 1987, vol. 16 (1), pp. 123-140.

(Continued)

*Primary Examiner* — Shafiqul Haq
(74) *Attorney, Agent, or Firm* — Audrey L. Bartnicki; Jennifer Walhsten, Weaver, Austin, Villeneuve & Sampson LLP

(57) ABSTRACT

An improved extractive reagent composition and method for extracting an immunosuppressant drug, such as sirolimus, tacrolimus or cyclosporine, from blood samples while yielding a test sample extract that has low vapor pressure and is compatible with immunoassay components. The inventive reagent composition comprises dimethyl sulfoxide (DMSO), at least one divalent metal salt and water. The sample extracts resulting from use of each of these combinations have low vapor pressure and are compatible with immunochemistry assays.

13 Claims, 5 Drawing Sheets

(56) References Cited

U.S. PATENT DOCUMENTS

| | | |
|---|---|---|
| 2006/0216770 A1 | 9/2006 | Kasper et al. |
| 2006/0257957 A1 | 11/2006 | Drengler et al. |
| 2008/0020401 A1 | 1/2008 | Grenier et al. |
| 2008/0160499 A1 | 7/2008 | Grenier et al. |
| 2008/0176756 A1 | 7/2008 | Siegel et al. |
| 2009/0325193 A1 | 12/2009 | Grenier et al. |
| 2009/0325197 A1 | 12/2009 | Drengler et al. |
| 2009/0325198 A1 | 12/2009 | Holets-McCormack et al. |

FOREIGN PATENT DOCUMENTS

| | | |
|---|---|---|
| CN | 1715923 | 1/2006 |
| EP | 293892 A2 | 12/1988 |
| EP | 440044 A1 | 8/1991 |
| EP | 0467606 A1 | 1/1992 |
| EP | 0471295 A1 | 2/1992 |
| EP | 753744 A2 | 1/1997 |
| EP | 693132 A1 | 12/1997 |
| EP | 0973805 A1 | 1/2000 |
| EP | 1244800 A1 | 3/2007 |
| EP | 2118657 A2 | 11/2009 |
| WO | WO/90/05008 A1 | 5/1990 |
| WO | WO9205179 A1 | 4/1992 |
| WO | WO9218527 A1 | 10/1992 |
| WO | WO9219745 A1 | 11/1992 |
| WO | WO9325533 A1 | 12/1993 |
| WO | WO9424304 A1 | 10/1994 |
| WO | WO9425022 A1 | 11/1994 |
| WO | WO9425072 A1 | 11/1994 |
| WO | WO9516691 A1 | 6/1995 |
| WO | WO9525812 A2 | 9/1995 |
| WO | WO9612018 A2 | 4/1996 |
| WO | WO9613273 A1 | 5/1996 |
| WO | WO9703654 A2 | 2/1997 |
| WO | WO/98/00696 A1 | 1/1998 |
| WO | WO9845333 A1 | 10/1998 |
| WO | WO/98/53315 A1 | 11/1998 |
| WO | 2000/37102 | 6/2000 |
| WO | WO0134816 A1 | 5/2001 |
| WO | 2001/42282 | 6/2001 |
| WO | WO2008054517 A2 | 5/2008 |
| WO | WO2008082974 A2 | 7/2008 |
| WO | WO2008082979 A2 | 7/2008 |
| WO | WO2008082982 A1 | 7/2008 |
| WO | WO2008082984 A2 | 7/2008 |
| WO | WO2009078875 A1 | 6/2009 |

OTHER PUBLICATIONS

Hayward C.M., et al., "Total Synthesis of Rapamycin via a Novel Titanium-Mediated Aldol Macrocyclization Reaction," Journal of the American Chemical Society, 1993, vol. 115, pp. 9345-9346.

Kricka L.J., et al., "Human Anti-Animal Antibody Interferences in Immunological Assays," Clinical Chemistry, 1999, vol. 45 (7), pp. 942-956.

Nicolaou et al., "Total Synthesis of Rapamycin", J. Am. Chem. Soc., 1993, 115, 4419-4420.

PCT International Search Report and Written Opinion for Application No. PCT/US07/88056, dated Aug. 25, 2008, 11 Pages, Abbott's Ref. 8299WOO1.

PCT International Search Report and Written Opinion for Application No. PCT/US07/88070, dated Oct. 8, 2008, 11 Pages, Abbott's Ref. 8571WOO1.

PCT International Search Report and Written Opinion for Application No. PCT/US07/88087, dated Sep. 24, 2008, 12 Pages, Abbott's Ref. 8572WOO1.

PCT International Search Report and Written Opinion for Application No. PCT/US07/88098, dated May 27, 2008, 7 pages, Abbott's Ref. 8573WOO1.

PCT International Search Report and Written Opinion for Application No. PCT/US07/88109, mailed on Sep. 24, 2008, 15 pages, Abbott's Ref. 8574WOO1.

PCT International Search Report and Written opinion for application No. PCT/US2007/10076, Mailed on Jul. 11, 2008, 11 pages, Abbott's Ref. 8166WOO1.

Romo D., et al., "Total Synthesis of (-)Rapamycin Using an Evans-Tishchenko Fragment Coupling", Journal of the American Chemical Society, 1993, vol. 115 (17), pp. 7906-7907.

Siegel R.W., et al., "Affinity Maturation of Tacrolimus Antibody for Improved Immunoassay Performance," Clinical Chemistry, 2008, vol. 54 (6), pp. 1008-1017.

Sinha N., et al., "Electrostatics in Protein Binding and Function," Current Protein and Peptide Science, 2002, vol. 3 (6), pp. 601-614.

Sinha N., et al., "Understanding Antibody-Antigen Associations by Molecular Dynamics Simulations: Detection of Important Intra- and Intermolecular Salt Bridges," Cell Biochem. Biophys., 2007, vol. 47 (3), pp. 361-375.

Supplementary European Search Report for Application No. EP07861291, mailed on Jan. 11, 2010, 11 pages.

Supplementary European Search Report for Application No. EP07869487, mailed on Mar. 19, 2010, 8 pages.

Supplementary European Search Report of EP Patent Application No. EP07865858, dated Apr. 1, 2010, 9 pages total.

Supplementary European Search Report of EP Patent Application No. EP07869508, dated Mar. 19, 2010, 11 pages total.

Tamura K., et al., "A Highly Sensitive Method to Assay FK-506 Levels in Plasma," Transplantation Proceedings Reprint, 1987, vol. 19 (6), pp. 23-29.

Uwatoko S., et al., "Characterization of C1q-Binding IgG Complexes in Systemic Lupus Erythematosus," Clinical Immunology and Immunopathology, 1984, vol. 30 (1), pp. 104-116.

Bouzas L., et al., "Determination of Everolimus in Whole Blood Using the Abbott IMx Sirolimus Microparticle Enzyme Immunoassay," Clinical Biochemistry, 2006, vol. 40 (1-2), pp. 132-136.

Colantonio D.A., et al., "Comparison of the CEDIA and MEIA Assays for the Measurement of Sirolimus in Organ Transplant Recipients," Clinical Biochemistry, 2007, vol. 40 (9-10), pp. 680-687.

Melnikova Y. I., et al., "Antigen-Binding Activity of Monoclonal Antibodies After Incubation With Organic Solvents", Biochemistry (Moscos), 2000, 65, 11, 1256-1265.

Simamora P., et al., "Solubilization of Sapamycin," International Journal of Pharmaceutics, 2001, vol. 213 (1-2), pp. 25-29.

Supplementary European Search Report for Application No. EP07861291, (8166EPO1), dated Mar. 23, 2011, 11 pages.

Supplementary European Search Report for Application No. EP07869484, (8299EPO1) dated Feb. 28, 2011, 8 pages.

U S Food and Drug Administration, Premarket Notification (510(k)) ARCHITECT Sirolimus, Clearances K070822, FUJIREBIO Diagnostics, Inc., 2007.

Supplementary European Search Report of EP Patent Application No. 07869499.9, dated Feb. 3, 2011, 6 pages total.

Supplementary European Search Report of EP Patent Application No. 07869484, dated Mar. 23, 2011, 8 pages total.

Murakami, et al., "On-chip micro-flow polystyrene bead-based immunoassay for quantitative detection of tacrolimus (FK506)," Analytical Biochemistry, 2004, vol. 334, pp. 111-116.

Clarke W., et al., "Immunoassays for therapeutic drug monitoring and clinical toxicology," Drug monitoring and clinical chemistry, 2004, 5, 95-112.

Grenier et al., "Multi-site Evaluation of the Sirolimus Assay* on the Abbott ARCHITECT Analyzer", Handout for the poster presented at the American Association for Clinical Chemistry Annual Meeting, 2006, pp. 1-4.

Kronquist K. E., et al., "Mechanism of alteration of the functional fraction of lipoprotein lipase in rat heart," Life Sci., 1980, 27(13), 1153-1158.

Le Meur Y., et al., "CYP3A5*3 influences sirolimus oral clearance in de novo and stable renal transplant recipients," Clin Pharmacol Ther., 2006, 80(1), 51-60.

Lee J. W., et al., "Tacrolimus (FK506): validation of a sensitive enzyme-linked immunosorbent assay kit for and application to a clinical pharmacokinetic study," Ther Drug Monit., 1997, 19(2), 201-207.

Wilson D., et al., "Multi-center evaluation of analytical performance of the microparticle enzyme immunoassay for sirolimus," Clin Biochem., 2006, 39(4), 378-386.

Search Report provided by State Intellectual Property Office of People's Republic of China for CN 200780102326.3 received on Jan. 31, 2013.

* cited by examiner

IMMUNOSUPPRESSANT DRUG EXTRACTION REAGENT FOR IMMUNOASSAYS

CROSS-REFERENCE TO RELATED APPLICATIONS

This is a divisional of U.S. patent application Ser. No. 11/490,624, filed on Jul. 21, 2006, now allowed, the contents of which are hereby incorporated by reference in their entirety.

FIELD OF THE INVENTION

This invention relates to diagnostic immunoassays to determine the concentration levels of an immunosuppressant drug in a patient blood sample, and in particular relates to use of an improved immunosuppressant drug extraction reagent composition.

BACKGROUND OF THE INVENTION

Immunosuppressant drugs such as sirolimus (also known as rapamycin), tacrolimus, everolimus, temsorolimus and cyclosporine are effective for the treatment of organ or tissue rejection following transplant surgery, of graft versus host disease and of autoimmune diseases in humans. During immunosuppressant drug therapy, monitoring the blood concentration levels of the immunosuppressant is an important aspect of clinical care because insufficient drug levels lead to graft (organ or tissue) rejection and excessive levels lead to undesired side effects and toxicities. Blood levels of immunosuppressant are therefore measured so drug dosages can be adjusted to maintain the drug level at the appropriate concentration. Diagnostic assays for determination of immunosuppressant blood levels have thus found wide clinical use.

Initially, the immunosuppressant must be extracted and separated from the other components of the patient sample. The bulk of the immunosuppressant drug in the patient sample is present in a complex with various "carrier" molecules, such as binding proteins. Sirolimus, tacrolimus and cyclosporine are found predominately in the red blood cells of patient specimens and are associated with specific binding proteins, FKBP for sirolimus and tacrolimus, and cyclophilin for cyclosporine. An accurate measurement of the total drug concentration in the specimen requires that the drug bound to the binding proteins be liberated prior to quantitation. Following its extraction from the binding proteins, the drug can be measured in a number of different ways, including by immunoassay or chromatography with absorbance or mass spectrophotometric detection.

Extraction of sirolimus from its binding proteins in blood is often accomplished by treatment with organic solvents, such as, acetonitrile, methanol, or diethyl ether. These solvents denature the binding proteins and liberate the drug. The use of organic solvents can be problematic, however, when an immunoassay is subsequently used to detect the liberated drug because most organic solvents that will quickly and completely denature the binding proteins are not compatible with immunoassays. They are either too harsh or they create a biphasic sample. Methanol has typically been employed to extract sirolimus, tacrolimus or cyclosporine from blood specimens before immunoassay. However, a careful balance must be achieved such that the methanol concentration is sufficient to liberate the drug from the binding protein, but not so great as to interfere with the subsequent immunoassay. The use of methanol and other typically used organic solvents create an additional problem because these solvents have higher vapor pressure than water. As a result, the extraction supernatant containing the immunosuppressant drug evaporates quickly which causes inaccuracy in the measurement of the drug concentration. The widely used methanol or acetonitrile solvents also create handling and disposal issues for the laboratories.

Immunoassays for immunosuppressant drugs are available in a variety of formats, but all use the binding of an antibody or binding protein (e.g. FKBP) to the immunosuppressant drug. A commonly used prior art immunoassay is an assay which involves the binding of a first antibody to the immunosuppressant and the binding of labeled immunosuppressant (e.g. acridinium-sirolimus) to the remaining free antibody binding sites, followed by quantitation by detection of the label. The effectiveness of these immunoassays is affected by the particular extraction and denaturing solvent for the immunosuppressant that is used.

It is an object of the invention to provide for use with immunoassays an improved immunosuppressant drug extraction reagent composition that has a low vapor pressure, miscibility with water, sufficient immunosuppressant denaturing power and compatibility with immunoassay reagents. Such an extraction reagent composition would be advantageous as well for non-immunoassay methods (e.g. chromatographic determinations) because the lower vapor pressure, sufficient denaturing power and water miscibility would make these methods easier to use.

SUMMARY OF THE INVENTION

The invention provides an improved extractive reagent composition and method for extracting an immunosuppressant drug, such as sirolimus, tacrolimus, everolimus, temsolorimus, zotarolimus, cyclosporine or analogs thereof, from blood samples while yielding a test sample extract that has low vapor pressure and is compatible with immunoassay components. The inventive reagent composition comprises dimethyl sulfoxide (DMSO), at least one divalent metal salt and water. The preferred reagent composition of the invention comprises DMSO and at least one of zinc sulfate, zinc acetate, zinc nitrate, zinc chloride, cadmium sulfate, copper sulfate and mixtures of two or more of these metal salts. A more preferred reagent composition comprises DMSO, the metal salt and at least one glycol having from two to six carbon atoms, which is preferably at least one of ethylene glycol (EG), propylene glycol (PG) or mixtures of EG and PG. Although DMSO, EG and PG are low vapor pressure solvents that are miscible in water and are in routine laboratory use, they have not been employed as protein denaturants but rather have often been added to protein and cell mixtures as stabilizing agents. In contrast, we have found that in the presence of divalent metal cations, DMSO at higher concentrations can serve as an effective protein denaturant to liberate immunosuppressant drugs. In addition, in the presence of divalent cations, lower concentrations of DMSO when mixed with EG or PG can also serve as an effective protein denaturant even though the concentrations of the solvents when used independently are not denaturing. The test sample extracts resulting from use of each of these combinations have low vapor pressure and are compatible with immunochemistry assays.

The invention also comprises a method for detecting concentration level of an immunosuppressant drug in a test sample comprising the steps of: (a) combining an extractive reagent composition comprising DMSO, a divalent metal salt and water with the test sample to form a test sample extract; (b) combining the test sample extract with at least one antibody or protein that is immunologically reactive with an immunosuppressant drug to form an assay mixture; (c) incubating the assay mixture under conditions suitable for formation of complexes between the antibody and the immunosuppressant drug, if any, which is present in the sample; and (d) detecting the presence of any complexes formed. Detection of the presence of complexes in step (d) can be carried out using an immunosuppressant to which a signal-generating compound has been attached to bind to the remaining free antibody binding sites on the analyte. A further embodiment provides that detection of the presence of complexes in step (d) is carried out using a detectable antibody that binds to the complexes formed in step (c).

The invention also comprises a reagent kit for an assay for blood levels of an immunosuppressant drug comprising a container containing the extractive reagent composition comprising DMSO, at least one divalent metal salt and water, and more preferably also comprising ethylene glycol, propylene glycol, or any suitable glycol analog or mixtures thereof. Preferably, the reagent kit further comprises a second container with at least one antibody or protein specific for the immunosuppressant drug. More preferably, the reagent kit contains a third container containing a control composition comprising an immunosuppressant drug, for example, an immunosuppressant selected from the group consisting of sirolimus, tacrolimus, everolimus, zotarolimus, cyclosporine and analogs thereof.

The invention has significant capability to provide higher sensitivity immunoassays for determining blood concentration levels of sirolimus, tacrolimus, everolimus, temsorolimsu, zotarolimus and cyclosporine. The inventive extractive reagent concentration allows more accurate measurement of the drug levels, while providing better ease of use for the clinical laboratory.

DETAILED DESCRIPTION OF THE INVENTION

I. General

Figure 1:
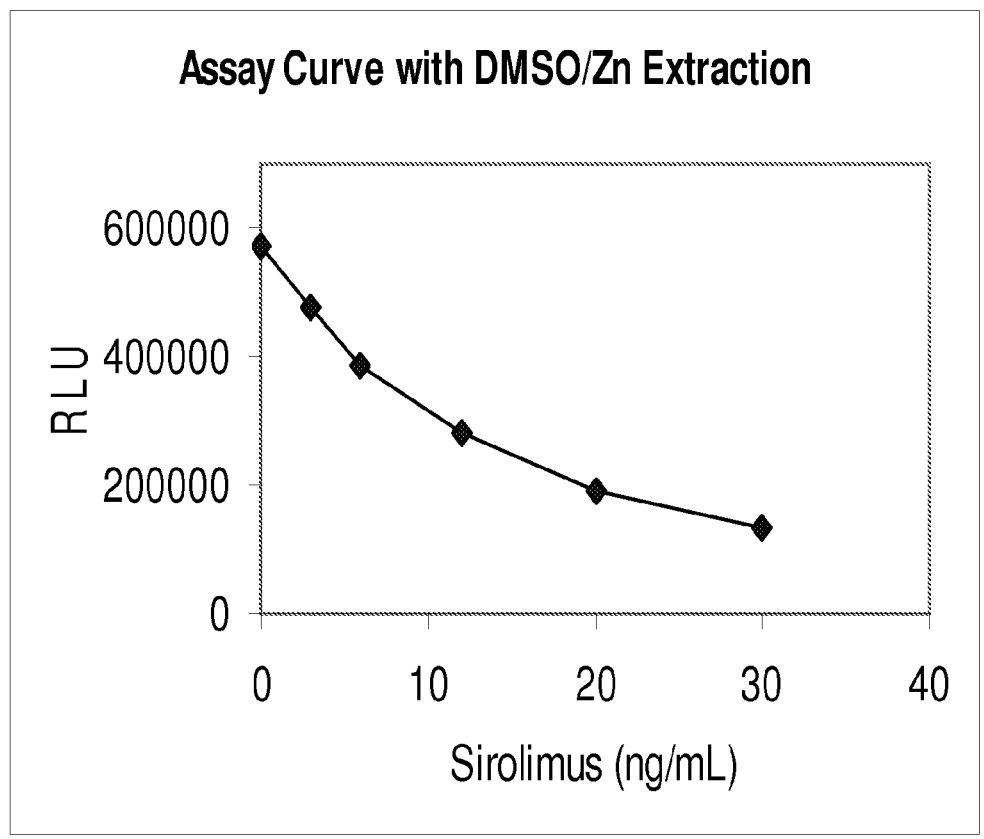
FIG. 1 shows experimental results on extraction of sirolimus from blood samples using DMSO and zinc sulfate.

The invention comprises extractive reagent compositions useful for the extraction and denaturation of immunosuppressant drugs such as sirolimus from a blood sample; methods for the quantification of immunosuppressant drug levels using the extractive reagent compositions of the invention; and diagnostic kits comprising the extractive reagent compositions of the invention. Preferred methods of the invention comprise immunoassays that use immunoreactive specific binding members, such as monoclonal or polyclonal antibodies, or binding proteins (e.g. FKBP) for the formation of complexes with the immunosuppressant drug analyte.

An "immunosuppressant drug" or "immunosuppressant", as used herein, refers to a therapeutic compound, either small molecule or antibody based, that has the same or similar chemical structure to either rapamycin (sirolimus), or cyclosporine, also known as cyclosporin A. Any known or hereafter developed analog of either rapamycin or cyclosporine is considered an immunosuppressant herein. Preferred immunosuppressants include sirolimus, tacrolimus, everolimus, temsorolimus, zotarolimus and cyclosporine. Tacrolimus and cyclosporine are calcineurin inhibitors that suppress early activation of the immune system's T lymphocytes through inhibition of cytokines such as interleukin 2. In contrast, the primary target of sirolimus, everolimus and zotarolimus is mammalian target of rapamycin (mTOR), a specific cell-cycle regulatory protein. The inhibition of mTOR leads to suppression of cytokine-driven T-lymphocyte proliferation.

The chemical formula of cyclosporine is in Formula A. The chemical formula of sirolimus is in Formula B. The chemical formula of the structural difference of everolimus (RAD) from sirolimus is in Formula C.

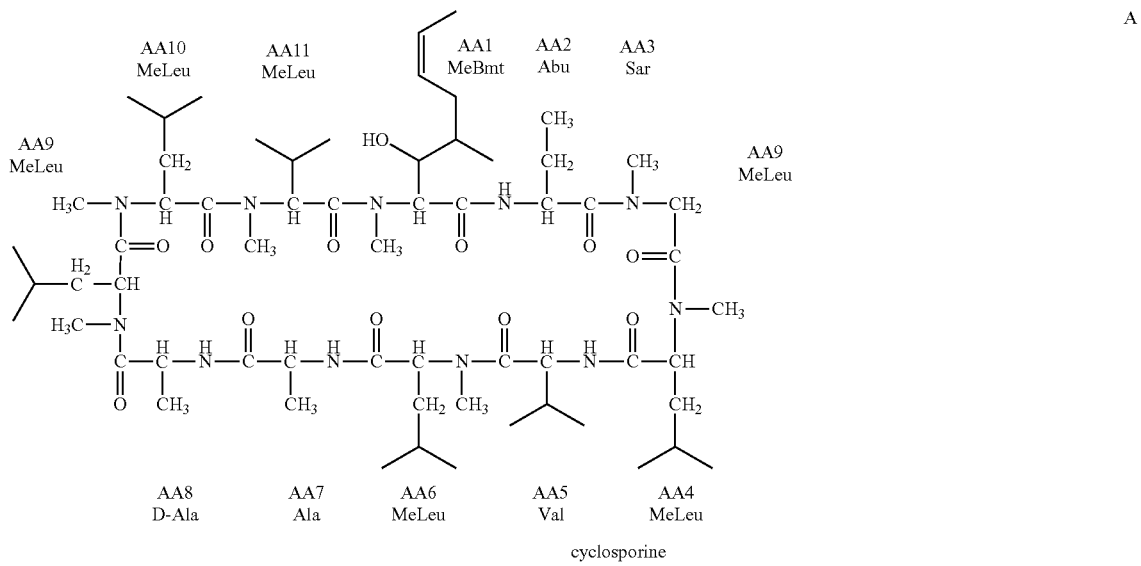

cyclosporine

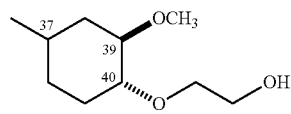

RAD

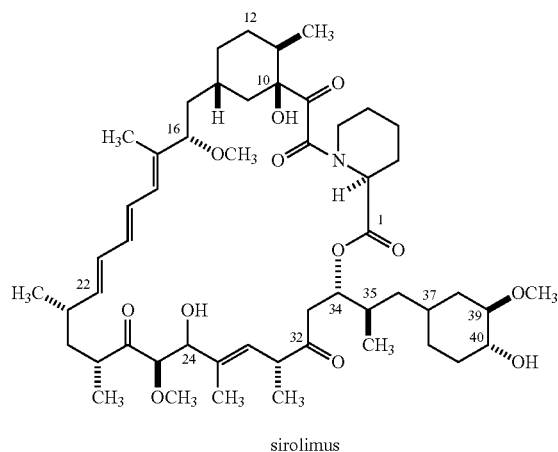

sirolimus

Numerous derivatives or analogs of cyclosporine have been prepared. The invention comprises extractive reagents, extractive methods, assays and assay kits for cyclosporine or any of its analogs.

Numerous derivatives or analogs of rapamycin have been prepared. For example, these include the preparation of ester mono- and di-ester derivatives of rapamycin (WO 92/05179); 27-oximes of rapamycin (EP0 467606); 42-oxo analog of rapamycin (U.S. Pat. No. 5,023,262); bicyclic rapamycins (U.S. Pat. No. 5,120,725); rapamycin dimers (U.S. Pat. No. 5,120,727); silyl ethers of rapamycin (U.S. Pat. No. 5,120,842); and arylsulfonates and sulfamates (U.S. Pat. No. 5,177,203). Rapamycin was recently synthesized in its naturally occurring enantiomeric form (K. C. Nicolaou et al., *J. Am. Chem. Soc.*, 1993, 115, 4419-4420; S. L. Schreiber, *J. Am. Chem. Soc.*, 1993, 115, 7906-7907; S. J. Danishefsky, *J. Am. Chem. Soc.*, 1993, 115, 9345-9346. The invention comprises extractive reagents, extractive methods, assays and assay kits for rapamycin or any of its analogs.

Another immunosuppressant analog of rapamycin is FK-506, also known as tacrolimus, which was isolated from a strain of *S. tsukubaensis*. FK-506's chemical formula is published in European Patent EP 0 293 892 B1. Analogs of FK-506 include the related natural products FR-900520 and FR-900523, which differ from FK-506 in their alkyl substituent at C-21, and were isolated from *S. hygroscopicus yakushimnaensis*. Another analog, FR-900525, produced by *S. tsukubaensis*, differs from FK-506 in the replacement of a pipecolic acid moiety with a proline group. The invention comprises extractive reagents, extractive methods, assays and assay kits for FK-506 or any of its analogs. Temsorolimus is another ester derivative of sirolimus which can be monitored with the invention.

ABT-578 [40-epi-(1-tetrazolyl)-rapamycin], known better today as zotarolimus, is a semi-synthetic macrolide triene antibiotic derived from rapamycin. Zotarolimus structure is shown in Formula D.

Formula D.
The isomers of zotarolimus

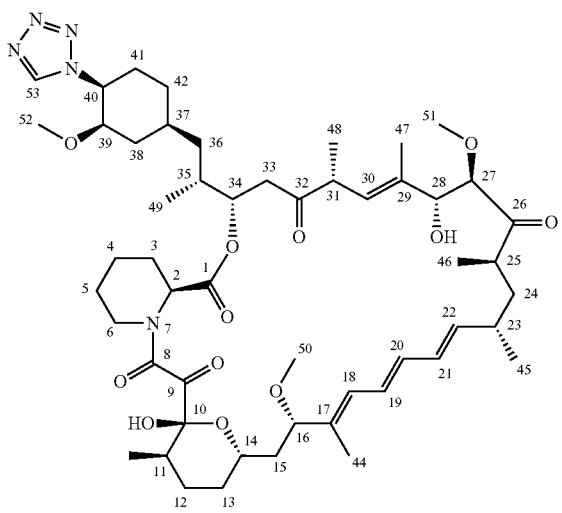

Pyran 1 (N-1 isomer)
(Ia)

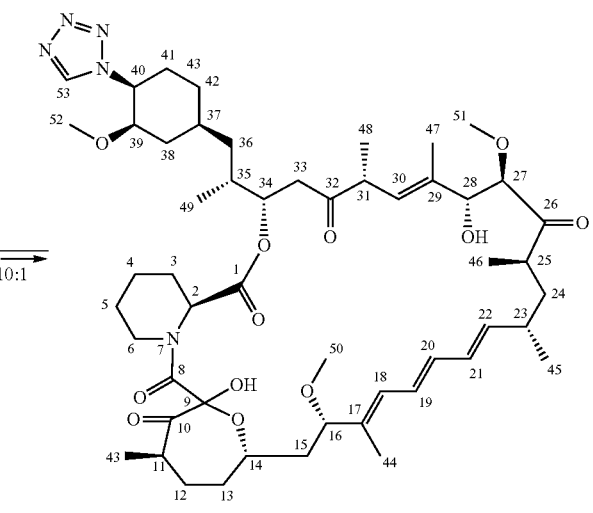

Oxepane 2
(Ib)

The invention comprises extractive reagents, extractive methods, assays and assay kits for zotarolimus or any of its analogs.

The term "test sample" refers to a component, tissue or fluid of a mammal's body that is the source of the immunosuppressant drug analyte. These components, tissues and fluids include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens. Preferably, the test sample is a human peripheral blood sample.

II. Extractive Reagent Compositions

The improved extractive reagent compositions of the invention comprise dimethyl sulfoxide (DMSO), at least one divalent metal salt and water. The preferred reagent composition of the invention comprises DMSO and at least one of zinc sulfate, zinc acetate, zinc nitrate, zinc chloride, cadmium sulfate and copper sulfate. A more preferred reagent composition comprises DMSO, at least one of ethylene glycol and propylene glycol, or any suitable glycol analog and the metal salt. The preferred compositions of the invention have vapor pressures less than water vapor pressure, as measured at 20 degrees centigrade and one atmosphere pressure, and are miscible with water.

Any suitable divalent metal salt that does not precipitate from the reagent composition of the invention can be used and salts of zinc are preferred. Exemplary suitable divalent metals include zinc, copper and cadmium. Applicants have not exhaustively tested all possible divalent metal cations, but have determined that tin and manganese sulfates were not suitable at the concentrations tested. The anion of the metal salt can be any suitable anion, including halides, nitrates, sulfates, sulfides, phosphates and acetates. The preferred metal salt is zinc sulfate.

The DMSO concentration, when used without EG or PG, in the extractive reagent composition is at least 50%, and preferably at least 80%, up to about 95% by volume of the extractive reagent composition. The metal salt concentration is at least 5 mM and concentrations up to 400 mM can be used. A preferred concentration range for the zinc salt is 30-75 mM. Use of high salt concentrations, for example above about 75 mM, might require use of a chelating compound, such as ethylene diamine tetraacetic acid, in a subsequent assay step to remove the excess metal. The extractive reagent compositions are made by any suitable mixing method to sufficiently mix the DMSO with water and dissolve the metal salt.

Applicants have found that when EG or PG is included in the extractive reagent composition, then lower concentrations of DMSO are more effective: In these preferred compositions, EG, PG or mixtures thereof are present in a concentration of at least 18%, and preferably about 25% to about 33% by volume of the extractive reagent composition, and DMSO is present in a concentration of at least 50% by volume of the extractive reagent composition.

II. Formation of the Test Sample Extract

The test sample extract is formed by any mixing technique at any desirable temperature to contact any chosen amount of the blood sample with the extractive reagent composition. Generally about 100 uL to about 600 uL of blood sample is mixed with about 200 uL to about 1200 uL of the extractive reagent composition for up to about five minutes. Preferably, the extraction of the immunosuppressant is accomplished by mixing 150 uL of blood sample with 300 uL of composition and vortexing vigorously for 5-10 seconds. Applicants prefer to perform the extraction by heating the extraction mixture to a temperature above room temperature in the range of about 30 degrees centigrade to about 50 degrees centigrade for about five minutes to about sixty minutes. After mixing, the resulting suspension is centrifuged for a suitable time at a suitable revolution rate to produce a supernatant phase and a precipitant phase. Preferably, the mixture is centrifuged at 13,000 rpm for 5 minutes to pellet the precipitant. After the centrifugation, the supernatant is separated using any suitable method. The supernatant is then assayed for the immunosuppressant using any suitable technique, including chromatography and immunoassay.

III. Immunoassays

In another aspect, the present invention relates to immunoassays that can be used for the qualitative identification and/or the quantification of the immunosuppressant drug in a test sample. The invention thus comprises a method for detecting concentration level of an immunosuppressant drug in a test sample comprising the steps of: (a) combining an extractive reagent composition comprising DMSO, at least one divalent metal salt with the test sample and water to form a test sample extract; (b) combining at least one antibody or protein capable of binding to an immunosuppressant drug with the test sample extract to form a test mixture; (c) incubating the test mixture under conditions suitable for formation of complexes between the antibody and the immunosuppressant drug, if any, which is present in the sample and is immunologically reactive with the antibody; and (d) detecting the presence of any complexes formed. The immunoassays of the invention can be conducted using any format known in the art, such as, but not limited to, a sandwich format, a competitive inhibition format (including both forward or reverse competitive inhibition assays) or in a fluorescence polarization format. The inventors have discovered that an excellent competitive inhibition immunoassay can be performed after using the extractive reagent compositions of the invention.

In immunoassays for the qualitative detection of an immunosuppressant drug in a test sample, at least one antibody or protein that binds to the immunosuppressant drug is contacted with at least one test sample or test sample extract suspected of containing or that is known to contain the immunosuppressant drug to form an antibody-drug or protein-drug immune complex. Any suitable antibodies or binding proteins (e.g. FKBP) that bind to the particular immunosuppressant can be used in the inventive immunoassays. Antibodies to each of sirolimus, tacrolimus, zotarolimus, cyclosporine and everolimus are known in the art, and any of these can be used. It is preferred to use the monoclonal antibody that is a component of Abbott Laboratories' commercially available IMX Sirolimus assay for measuring sirolimus.

The preferred antibody for detection of sirolimus can be produced as follows. Female RBf/Dnj mice are administered 3 monthly boosts of a sirolimus-27-CMO-tetanus toxoid immunogen followed by an immunization with sirolimus-42-HS-tetanus toxoid preparation on the 4th month. Seven months later, an intrasplenic pre-fusion boost is administered to the animal using the sirolimus-27-CMO-tetanus toxoid immunogen 3 days prior to the fusion. Splenic B-cells are then isolated and used in a standard PEG fusion with the SP2/0 myeloma. Confluent cultures are screened for anti-sirolimus activity 10-14 days later in a microtiter EIA and positive cultures are then cloned using limiting dilution cloning technique. The resulting clones are isolated and scaled up in IMDM w/FBS (Invitrogen) tissue culture medium and the secreted antibody is affinity purified using Protein A.

The preferred sirolimus antibody described above is also effective for use in immunoassays for everolimus and zotarolimus. A preferred antibody for use in immunoassays for tacrolimus is described in M. Kobayashi et al., "A Highly Sensitive Method to Assay FK-506 Levels in Plasma", at pp 23-29 of "FK-506 A Potential Breakthrough in Immunosuppression", *A Transplantation Proceedings Reprint*, Supplement 6, Vol. XIX, October, 1987, Editors T. Starzl, L. Makowka and S. Todo, published by Grune & Stratton, Inc., Philadelphia, Pa. A preferred antibody for use in immunoassays for cyclosporin is the monoclonal antibody that is a component of Abbott Laboratories' commercially available AxSym cyclosporine assay for measuring cyclosporine.

The antibody-drug immune complexes can then detected using any suitable technique. For example, the antibody can be labeled with a detectable label to detect the presence of the antibody-drug complex. Any suitable label can be used. The selection of a particular label is not critical, but the chosen label must be capable of producing a detectable signal either by itself or in conjunction with one or more additional substances.

Useful detectable labels, their attachment to antibodies or to other binding proteins and detection techniques therefore are known in the art. Any detectable label known in the art can be used. For example, the detectable label can be a radioactive label, such as, $^3$H, $^{125}$I, $^{35}$S, $^{14}$C, $^{32}$P, $^{33}$P, an enzymatic label, such as horseradish peroxidase, alkaline peroxidase, glucose 6-phosphate dehydrogenase, etc., a chemiluminescent label, such as, acridinium derivatives, luminol, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemi* (1996), which is a combined handbook and catalogue published by Molecular Probes, Inc., Eugene, Oreg., each of which is incorporated herein by reference. Preferred labels for use with the invention are chemiluminscent labels such as acridinium-9-carboxamide. Additional detail can be found in Mattingly, P. G., and Adamczyk, M. (2002) Chemiluminescent N-sulfonylacridinium-9-carboxamides and their application in clinical assays, in *Luminescence Biotechnology: Instruments and Applications* (Dyke, K. V., Ed.) pp 77-105, CRC Press, Boca Raton.

The detectable label can be bound to the analyte or antibody either directly or through a coupling agent. An example of a coupling agent that can be used is EDAC (1-ethyl-3-(3-dimethylaminopropyl) carbodiimide, hydrochloride) that is commercially available from Sigma-Aldrich (St. Louis, Mo.). Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

Alternatively, a second antibody that binds to immunosuppressant and that contains a detectable label can be added to the test sample or test sample extract and used to detect the presence of the antibody-drug complex. Any suitable detectable label can be used in this embodiment.

In immunoassays for the quantitative detection of an immunosuppressant, such as a preferred sandwich type format, at least two antibodies are employed to separate and quantify the drug in the test sample or test sample extract. More specifically, the at least two antibodies bind to different parts of the drug forming an immune complex which is referred to as a "sandwich". Generally, one or more antibodies can be used to capture the immunosuppressant in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, it is preferred that both antibodies binding to the drug are not diminished by the binding of any other antibody in the assay to its respective binding site. In other words, antibodies should be selected so that the one or more first antibodies brought into contact with a test sample or test sample extract suspected of containing an immunosuppressant do not bind to all or part of the binding site recognized by the second or subsequent antibodies, thereby interfering with the ability of the one or more second detection antibodies to bind to the drug. In a sandwich assay, the antibodies, preferably, the at least one capture antibody, are used in molar excess amounts of the maximum amount of drug expected in the test sample or test sample extract. For example, from about 5 μg/mL to about 1 mg/mL of antibody per mL of solid phase containing solution can be used.

In one embodiment, the at least one first capture antibody can be bound to a solid support which facilitates the separation of the first antibody-drug complex from the test sample. The solid support or "solid phase" used in the inventive immunoassay is not critical and can be selected by one skilled in the art. A solid phase or solid support, as used herein, refers to any material that is insoluble, or can be made insoluble by a subsequent reaction. Useful solid phases or solid supports are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (a registered trademark of Abbott Laboratories, Abbott Park, Ill.), which are red blood cells "fixed" by pyruvic aldehyde and formaldehyde, and others. Suitable methods for immobilizing peptides on solid phases include ionic, hydrophobic, covalent interactions and the like. The solid phase can be chosen for its intrinsic ability to attract and immobilize the capture reagent. Alternatively, the solid phase can comprise an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay.

Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind the drug. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

It is within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces.

After the test sample extract suspected of containing or containing the immunosuppressant is brought into contact with the at least one first capture antibody, the resulting mixture is incubated to allow for the formation of a first capture antibody (or multiple antibody)-drug complex. The incubation can be carried out at any suitable pH, including a pH of from about 4.5 to about 10.0, at any suitable temperature, including from about 2° C. to about 45° C., and for a suitable time period from at least about one (1) minute to about eighteen (18) hours, preferably from about 4-20 minutes, most preferably from about 17-19 minutes.

After formation of the labeled complex, the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of drug in the test sample is determined by use of a standard curve that has been generated using serial dilutions of immunosuppressant drug of known concentration. Other than using serial dilutions of the drug, the standard curve can be generated gravimetrically, by mass spectroscopy and by other techniques known in the art.

In a preferred forward competitive format, an aliquot of labeled drug or analogue thereof of a known concentration is used to compete with the drug present in a test sample for binding to the antibody. In a forward competition assay, an immobilized antibody can either be sequentially or simultaneously contacted with the test sample and a labeled drug or drug analogue thereof. The drug or drug analogue can be labeled with any suitable detectable label, including those detectable labels discussed above. In this assay, the antibody of the present invention can be immobilized on to a solid support using the techniques discussed previously herein. Alternatively, the antibody can be coupled to an antibody, such as an antispecies antibody, that has been immobilized on to a solid support, such as a microparticle.

The labeled drug or drug analogue, the test sample extract and the antibody are incubated under conditions similar to those described above in connection with the sandwich assay format. Two different types of antibody-drug complexes are then generated. Specifically, one of the antibody-drug complexes generated contains a detectable label while the other antibody-drug complex does not contain a detectable label. The antibody-drug complex can be, but does not have to be, separated from the remainder of the test sample extract prior to quantification of the detectable label. Regardless of whether the antibody-drug complex is separated from the remainder of the test sample, the amount of detectable label in the antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

The antibody-drug complex can be separated from the test sample by binding the antibody to a solid support, such as the solid supports discussed above in connection with the sandwich assay format, and then removing the remainder of the test sample from contact with the solid support.

In a reverse competition assay, an immobilized immunosuppressant drug or analogue thereof can either be sequentially or simultaneously contacted with a test sample or test sample extract and at least one labeled antibody or labeled protein. The antibody or protein can be labeled with any suitable detectable label, including those detectable labels discussed above. The drug or drug analogue can be bound to a solid support, such as the solid supports discussed above in connection with the sandwich assay format.

The immobilized drug or drug analogue, test sample or test sample extract, and at least one labeled antibody or labeled protein are incubated under conditions similar to those described above in connection with the sandwich assay format. Two different types of antibody-drug or protein-drug complexes are then generated. Specifically, one of the antibody-drug (or protein-drug) complexes generated is immobilized and contains a detectable label while the other antibody-drug (or protein-drug) complex is not immobilized and contains a detectable label. The non-immobilized antibody-drug complex and the remainder of the test sample or test sample extract are removed from the presence of the immobilized antibody-drug complex through techniques known in the art, such as washing. Once the non-immobilized antibody-drug complex is removed, the amount of detectable label in the immobilized antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

In a fluorescence polarization assay, in one embodiment, an antibody or functionally active fragment thereof is first contacted with an unlabeled test sample containing the immunosuppressant drug to form an unlabeled antibody-drug complex. The unlabeled antibody-drug complex is then contacted with a fluorescently labeled drug or analogue thereof. The labeled drug or drug analogue competes with any unlabeled drug in the test sample for binding to the antibody or functionally active fragment thereof. The amount of labeled antibody-drug complex formed is determined and the amount of drug in the test sample determined via use of a standard curve.

In a further aspect of the present invention, there is disclosed a method for detecting concentration level of an immunosuppressant drug in a test sample comprising the steps of: (a) combining an extractive reagent composition comprising DMSO, at least one divalent metal salt and water with the test sample to form a test sample extract; (b) combining at least one antibody or protein capable of binding to an immunosuppressant drug with the test sample extract to form a mixture; (c) incubating the mixture under conditions suitable for formation of complexes between the antibody and the immunosuppressant drug, if any, which is present in the sample and is immunologically reactive with the antibody; and (d) detecting the presence of any antibody-immunosuppressant drug complexes formed.

IV. Other Immunosuppressant Assays

Any other alternative measurement method for the concentration of immunosuppressant can also be used with the inventive extractive reagent compositions. For example, the drug content can be determined by a mass spectrometry based method, such as the rapid liquid chromatography—tandem mass spectrometry technique described in N. Brown et al., "Low Hematocrit and Serum Albumin Concentrations Underlie the Overestimation of Tacrolimus Concentrations by Microparticle Enzyme Immunoassay versus Liquid Chromatography—Tandem Mass Spectrometry", *Clinical Chemistry.* 2005; 51:586-592.

V. Instrumentation

Any suitable instrumentation or automation can be used in the performance of the contact of the extractive reagent composition with the blood sample and in the performance of the drug concentration level assay. It is preferred to carry out the assay in an automated fashion, such as on the Architect® (a registered trademark of Abbott Laboratories, Abbott Park, Ill.) system, which uses chemiluminescense detection of sandwich hybridization and competitive immunoassays. The assay can also be carried out in a miniaturized format, such as in a Lab-on-a-Chip device and system.

VI. Immunoassay Kits

In another aspect, the invention comprises immunoassay kits for the detection of an immunosuppressant drug of the same or similar chemical structure to either sirolimus or cyclosporine, preferably selected from the group consisting of sirolimus, tacrolimus, everolimus, zotarolimus, cyclosporine and analogs thereof, which kits comprise an extractive reagent composition of the invention. These kits may also include an antibody capture reagent or antibody indicator reagent useful to carry out a sandwich immunoassay. Preferred kits of the invention comprise containers containing, respectively, at least one antibody or protein capable of binding specifically to at least one immunosuppressant drug selected from the group consisting of sirolimus, tacrolimus, everolimus, zotarolimus and cyclosporine; an extractive reagent composition comprising 50% DMSO by volume of the extractive reagent composition, 30%-33% EG, PG or mixtures thereof by volume of the extractive reagent composition, water and zinc sulfate at a concentration of at least 5 mM; and a control composition comprising at least one immunosuppressant drug selected from the group consisting of sirolimus, tacrolimus, everolimus, zotarolimus, cyclosporine or analogs thereof.

Any suitable control composition for the particular immunosuppressant drug assay can be included in the kits of the invention. The control compositions generally comprise the actual immunosuppressant to be assayed for along with any desirable additives. For example, the control composition for tacrolimus can be the control compositions described in U.S. Pat. No. 5,338,684, Grenier et al.

VII. Examples

Example 1

This example illustrates the use of DMSO in combination with zinc sulfate to extract sirolimus from binding proteins in blood samples. The extracted sirolimus is measured with an immunoassay.

The extractive reagent composition was prepared at final concentrations of 86% DMSO, 14% water and 40 mM zinc sulfate. Extraction of the blood sirolimus samples was accomplished by mixing 100 uL of blood sample with 200 uL of the reagent composition and vortexing vigorously for 5-10 seconds. The resulting suspension was centrifuged at 13,000 rpm for 5 minutes to pellet the precipitate and the supernatant extract was assayed for sirolimus as follows. The assay was executed on an automated ARCHITECT i2000 analyzer (Abbott Laboratories, Abbott Park, Ill.) by:

1. Mixing 10-40 uL of the sample extract with 50 uL of microparticles coated with goat anti-mouse antibody (from Sigma, St. Louis, Mo.) and mouse anti-sirolimus antibody (prepared as described below).

2. Incubating the reaction mixture for approximately 18 minutes at 33-38 degrees C. The sirolimus in the sample binds the anti-sirolimus antibody on the microparticles.

3. Adding 20 uL of acridinium-sirolimus detector molecule to the reaction mixture.

4. Incubating the reaction mixture for approximately 4 minutes at 33-38 degrees C. The acridinium-sirolimus molecule binds free anti-sirolimus binding sites.

5. Washing the microparticles with a phosphate buffer.

6. Adding Pre-trigger (acid solution) and Trigger (basic solution) to cause the captured acridinium-sirolimus label to emit light, which is measured by the instrument.

The sirolimus binding antibody was produced as follows: Female RBf/Dnj mice were administered 3 monthly boosts of a sirolimus-27-CMO-tetanus toxoid immunogen followed by an immunization with sirolimus-42-HS-tetanus toxoid preparation on the 4th month. Seven months later, an intrasplenic pre-fusion boost was administered to the animal using the sirolimus-27-CMO-tetanus toxoid immunogen 3 days prior to the fusion. Splenic B-cells were isolated and used in a standard PEG fusion with the SP2/0 myeloma. Confluent cultures were screened for anti-sirolimus activity 10-14 days later in a microtiter EIA and positive cultures were cloned using limiting dilution cloning technique. Isolated clones were scaled up in IMDM w/FBS (Invitrogen) tissue culture medium and secreted antibody was affinity purified using Protein A.

The response curve data are shown in Table 1 and FIG. 1 and demonstrate that sirolimus was liberated from binding proteins with the DMSO/zinc sulfate composition.

TABLE 1

| Sirolimus (ng/mL) | RLUs |
|---|---|
| 0 | 573660 |
| 3 | 474794 |

TABLE 1-continued

| Sirolimus (ng/mL) | RLUs |
| --- | --- |
| 6 | 387857 |
| 12 | 279516 |
| 20 | 191208 |
| 30 | 131426 |

Signal measurements in Table 1 are in RLUs (Relative Light Units). RLUs are the designation for the optical unit of measurement utilized on the ARCHITECT systems. The ARCHITCT optics system is essentially a photomultiplier tube (PMT) that performs photon counting on the light emitted by the chemiluminescent reaction. The amount of light generated by the chemiluminescent reaction is proportional to the amount of acridinium tracer present in the reaction mixture, and thereby allows quantitation of the patient sample analyte that is also proportional to the amount of acridinium remaining in the reaction mixture at the time the chemiluminescent reaction occurs.

The term Relative Light Units comes from the relation of the photon counting to a certain amount of acridinium. Each optics module is calibrated with a set of acridinium standards. When the chemiluminescent reaction occurs, light is emitted and the photons are measured over a 3 second time period. The PMT converts the photons counted to digital signal, which is then sent to a circuit board for processing. The optics circuit board converts the digital signal from the PMT to an analog signal that is proportional to the photons counted, which is in turn proportional to the amount of acridinium present. This analog signal is then further processed to produce an RLU value. This relationship was established to produce a standard for calibration of the optics module, where the different acridinium standards have RLU values assigned to them. So, while the RLU unit itself is arbitrary, it is proportional (i.e., relative) to a certain amount of acridinium.

Example 2

This example illustrates the utility of varying zinc concentrations in the composition.

Figure 2:
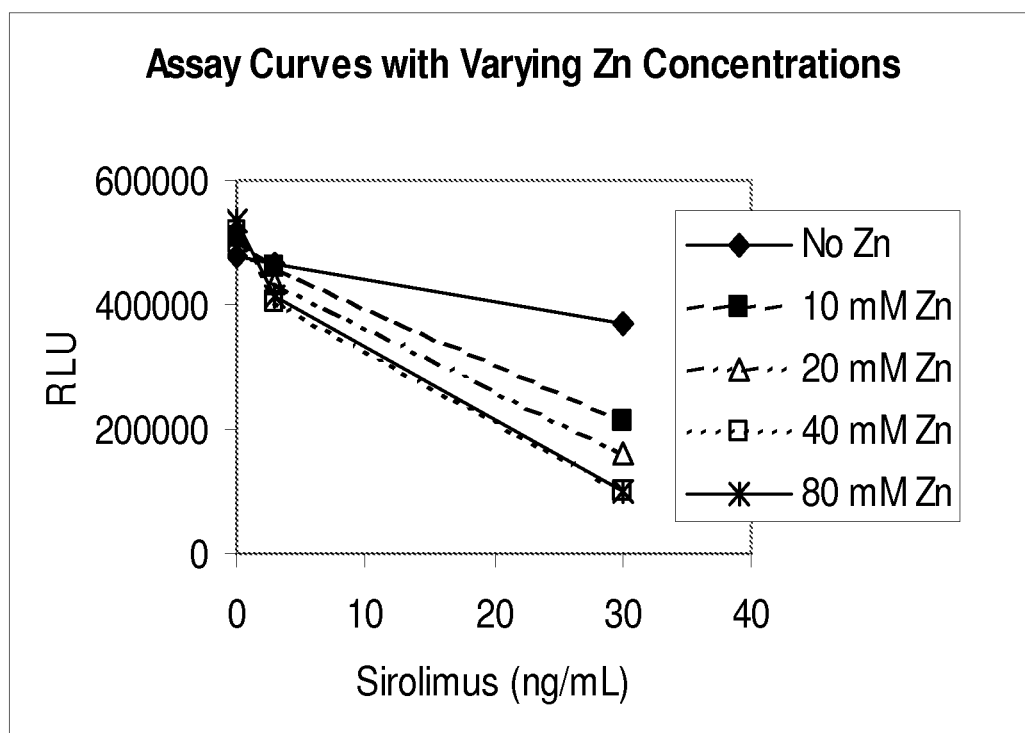
FIG. 2 shows experimental results on extraction of sirolimus from blood samples using DMSO and varying amounts of zinc sulfate.

The composition was prepared at varying final concentrations of zinc sulfate (0, 10, 20, 40 and 80 mM) in 90% DMSO and 10% water. Extraction of the blood sirolimus samples was accomplished by mixing 400 uL of blood sample with 800 uL of composition and vortexing vigorously for 5-10 seconds. The resulting suspension was centrifuged at 13,000 rpm for 5 minutes to pellet the precipitant and the supernatant was assayed for sirolimus. The sirolimus assay was performed as in Example 1. The test data are shown in Table 2 and FIG. 2 and illustrate that the liberation of sirolimus from binding proteins is improved by the addition of the zinc salt. Applicants have also tested and determined that zinc chloride, zinc nitrate, and zinc acetate are also efficacious.

TABLE 2

| Sirolimus | RLU | | | | |
| --- | --- | --- | --- | --- | --- |
| (ng/mL) | No Zn | 10 mM Zn | 20 mM Zn | 40 mM Zn | 80 mM Zn |
| 0 | 477005 | 509875 | 503822 | 517429 | 532760 |
| 3 | 464256 | 461998 | 435120 | 403487 | 414074 |
| 30 | 367821 | 214924 | 161065 | 99300 | 100777 |

Example 3

This example illustrates the utility of different divalent cations in the composition.

The extraction composition was prepared at different final concentrations of metal salts (zinc sulfate, cadmium sulfate, copper sulfate, tin sulfate and manganese sulfate) and DMSO as shown in the table below (remaining volume was water). Extraction of the blood sirolimus samples was accomplished by mixing 200 uL of blood sample with 400 uL of composition and vortexing vigorously for 5-10 seconds. The resulting suspension was centrifuged at 13,000 rpm for 5 minutes to pellet the precipitant and the supernatant was assayed for sirolimus. The sirolimus assay was performed as in Example 1. The example data are shown in Table 3 and demonstrate that metal salts other than zinc can also be utilized.

TABLE 3

| | DMSO | | | | |
| --- | --- | --- | --- | --- | --- |
| | 90% | 90% | 50% | 90% | 90% |
| | | | Metal Salt | | |
| Sirolimus (ng/mL) | 40 mM Zn RLUs | 50 mM Cd RLUs | 50 mM Cu RLUs | 20 mM Sn RLUs | 20 mM Mn RLUsl |
| 0 | 550492 | 536394 | 523472 | 517375 | 524178 |
| 3 | 441164 | 413887 | 430245 | 475927 | 469885 |
| 30 | 107957 | 89515 | 126515 | 222690 | 220562 |

Example 4

This example illustrates the utility of varying ratios of DMSO and EG in the extractive reagent composition.

Figure 3:
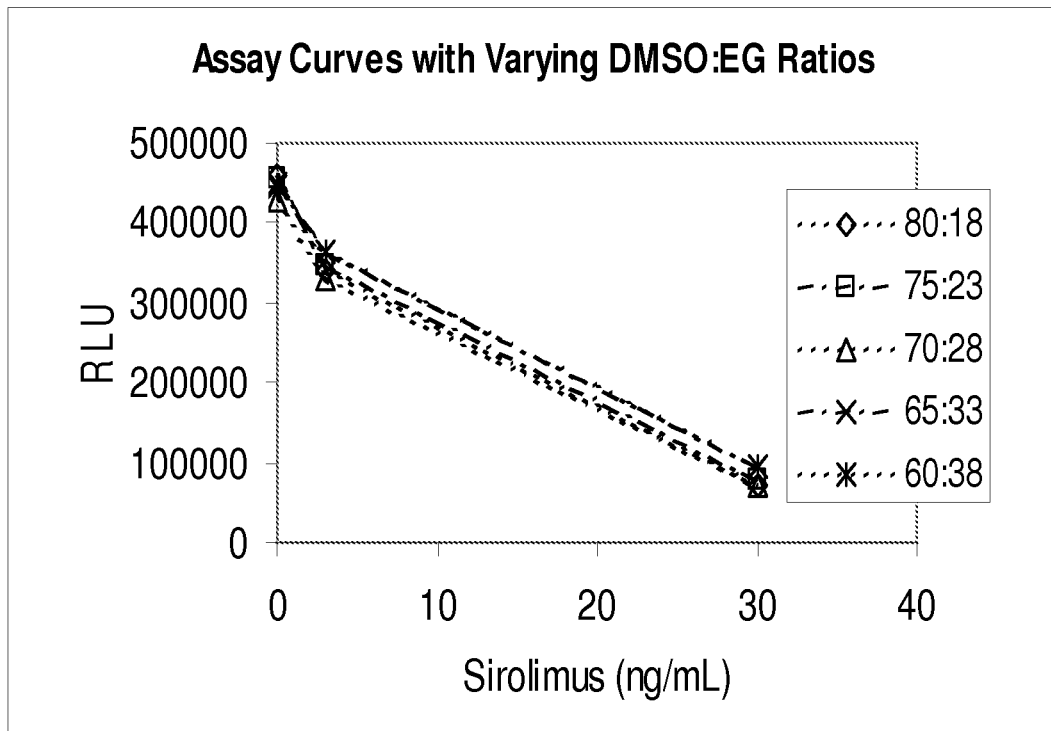
FIG. 3 shows experimental results on extraction of sirolimus from blood samples using DMSO, EG and zinc sulfate.

The composition was prepared at different final concentration ratios of DMSO and ethylene glycol (percent DMSO and percent ethylene glycol were 80:18, 75:23, 70:28, 65:33 and 60:33, respectively). All compositions had 2% water and 40 mM zinc sulfate. Extraction of the blood sirolimus samples was accomplished by mixing 150 uL of blood sample with 300 uL of composition and vortexing vigorously for 5-10 seconds. The resulting suspension was centrifuged at 13,000 rpm for 5 minutes to pellet the precipitant and the supernatant was assayed for sirolimus. The sirolimus assay was performed as in Example 1. The example data are shown in Table 4 and FIG. 3 and demonstrate that sufficient denaturing power can be maintained when the concentration of DMSO is decreased if the ethylene glycol concentration is increased.

TABLE 4

| Sirolimus | RLUs with varying DMSO:EG Ratios | | | | |
| --- | --- | --- | --- | --- | --- |
| (ng/mL) | 80:18 | 75:23 | 70:28 | 65:33 | 60:38 |
| 0 | 457694 | 454223 | 428721 | 450344 | 446482 |
| 3 | 340579 | 346026 | 330247 | 364041 | 363857 |
| 30 | 70582 | 78831 | 72669 | 95479 | 94442 |

Concentrations of DMSO or ethylene glycol that are not at all or only marginally efficacious when used alone (e.g. 65% DMSO or 33% ethylene glycol) are highly effective in combination. Propylene glycol can be substituted for ethylene glycol in the DMSO:ethylene glycol mixtures (data not shown). The DMSO:ethylene glycol mixtures have the additional advantage of increased solubility for zinc sulfate.

Example 5

This example illustrates the improvement in the sirolimus extraction efficiency achieved by heating the extraction mixture.

The DMSO-based composition was prepared at final concentrations of 70% DMSO, 28% ethylene glycol, 2% water and 46 mM zinc sulfate. Extraction of the blood sirolimus samples was accomplished by mixing 150 uL of blood sample with 300 uL of composition, vortexing vigorously for 5-10 seconds and incubating at different temperatures for 15 minutes. The resulting suspension was centrifuged at 13,000 rpm for 5 minutes to pellet the precipitant and the supernatant was assayed for sirolimus. The sirolimus assay was performed as in Example 1.

Figure 4:
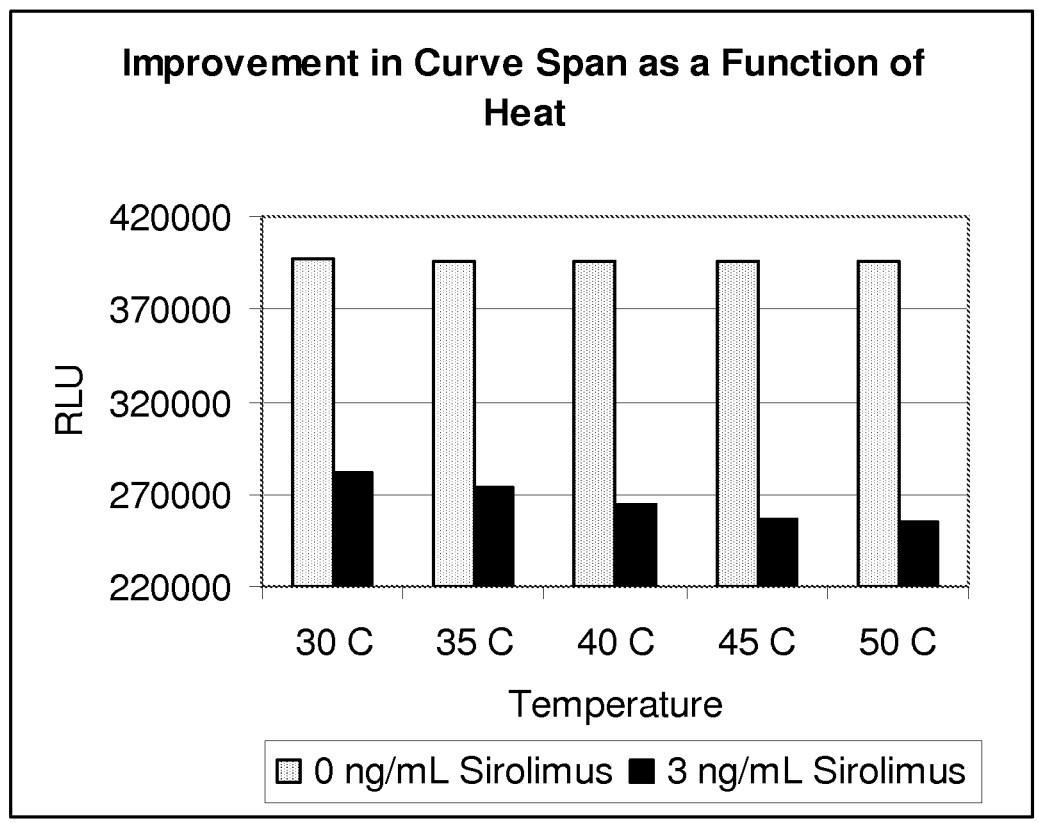
FIG. 4 shows experimental results on heating the extraction mixture from blood samples and the extractive reagent composition of the invention.

The example data are shown in Table 5 and FIG. 4 and demonstrate that more efficient liberation of sirolimus occurs when the extraction mixture is heated (i.e. the difference between the 0 ng/mL calibrator and the 3 ng/mL calibrator increases with increasing temperature).

TABLE 5

| | RLUs as a Function of Temperature | | | | |
|---|---|---|---|---|---|
| | 30 C. | 35 C. | 40 C. | 45 C. | 50 C. |
| 0 ng/mL Sirolimus | 397353 | 395993 | 396009 | 395694 | 395957 |
| 3 ng/mL Sirolimus | 281375 | 273856 | 264768 | 256660 | 254426 |

Example 6

This example illustrates the minimal evaporation of a DMSO-based extraction composition compared to a typical methanol-based extraction composition.

Figure 5:
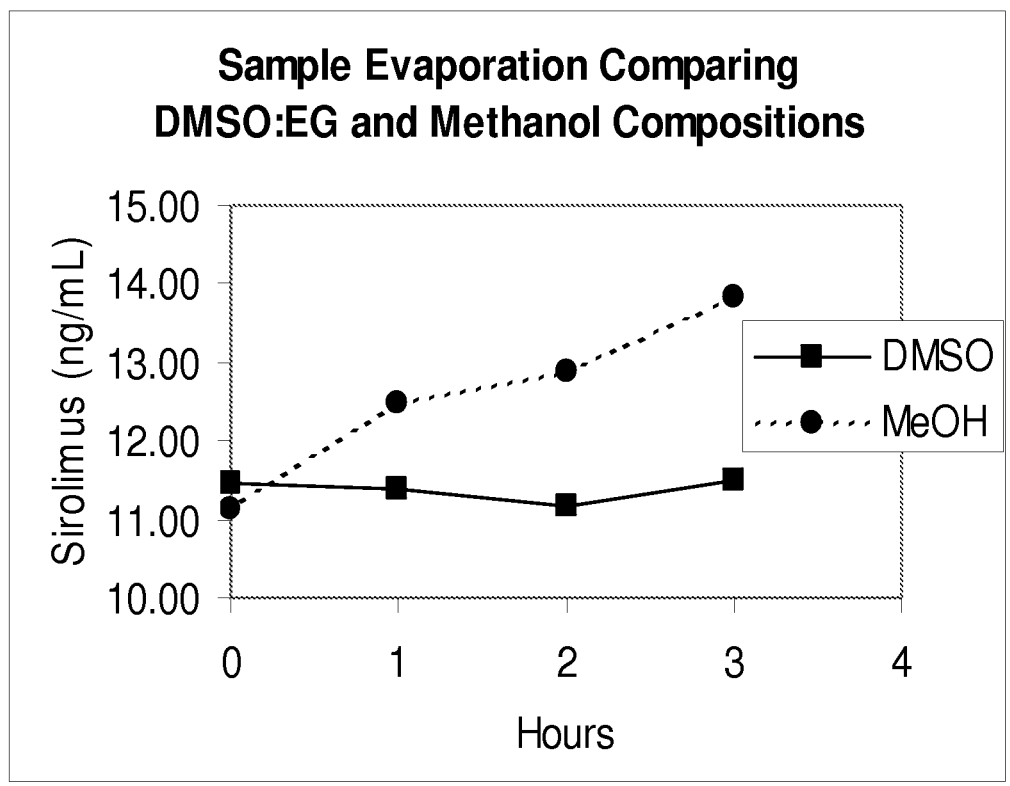
FIG. 5 shows a comparison of sample extract evaporation rates resulting from use of a prior art methanol denaturant and from use of the invention.

The DMSO-based composition was prepared at final concentrations of 70% DMSO, 28% ethylene glycol, 2% water and 46 mM zinc sulfate. The methanol-based composition was prepared at final concentrations of 80% methanol, 18% ethylene glycol, 2% water and 50 mM zinc sulfate. Extraction of the blood sirolimus samples with either composition was accomplished by mixing 125 uL of blood sample with 250 uL of composition and vortexing vigorously for 5-10 seconds. The DMSO-based composition extraction mixture was incubated at 42° C. for 10 minutes and the methanol-based composition extraction mixture was incubated at room temperature for 10 minutes. The extraction mixtures were centrifuged at 13,000 rpm for 5 minutes to pellet the precipitant and the supernatants were decanted in the sample cups used in the ARCHITECT i2000 analyzer. A set of samples was tested for evaporation immediately (time zero) and at 1, 2 and 3 hours after decanting into the sample cup (samples allowed to sit at room temperature, approximately 22° C.). The test data are shown in Table 6 and FIG. 5 and illustrate the rapid evaporation of methanol-based compositions, which is manifested as higher sirolimus concentrations. In less than 2 hours, the error in the sirolimus concentration had exceeded 10% with the methanol-based composition, but essentially no change in concentration had occurred with the DMSO-composition. The error in the sirolimus concentration would be greater if the humidity was lower or if the incubation temperature was higher (some immunochemistry assay analyzers incubate samples at temperatures near 37° C.).

TABLE 6

| | Sirolimus (ng/mL) | |
|---|---|---|
| Hours | DMSO | MeOH |
| 0 | 11.47 | 11.14 |
| 1 | 11.37 | 12.47 |
| 2 | 11.18 | 12.88 |
| 3 | 11.50 | 13.83 |

The above-described exemplary embodiments are intended to be illustrative in all respects, rather than restrictive, of the present invention. Thus, the present invention is capable of implementation in many variations and modifications that can be derived from the description herein by a person skilled in the art. All such variations and modifications are considered to be within the scope and spirit of the present invention as defined by the following claims.

What is claimed is:

1. An extractive reagent composition comprising dimethyl sulfoxide, a glycol, and at least one divalent metal salt of zinc and water, wherein the dimethyl sulfoxide is at least about 50% of the extractive reagent composition, the divalent metal salt of zinc is at a concentration of about 30 mM to about 75 mM in the extractive reagent composition, and the glycol is selected from the group consisting of ethylene glycol, propylene glycol, glycol analogs and mixtures thereof.

2. The extractive reagent composition of claim 1 wherein the divalent metal salt of zinc is selected from the group consisting of zinc sulfate, zinc acetate, zinc nitrate, zinc chloride, and mixtures of two or more of these metal salts.

3. The extractive reagent composition of claim 1 wherein the extractive reagent composition comprises zinc sulfate.

4. The extractive reagent composition of claim 2 wherein the extractive reagent composition comprises zinc sulfate.

5. A test sample extract comprising dimethyl sulfoxide of at least about 33% by volume of the extract, at least one divalent metal salt of zinc, an antibody that binds to at least one immunosuppressant drug, and water.

6. The test sample extract of claim 5, wherein the test sample extract comprises an immunosuppressant drug.

7. The test sample extract of claim 5, wherein the immunosuppressant drug is selected from the group consisting of sirolimus, tacrolimus, everolimus, zotarolimus and cyclosporine.

8. The test sample extract of claim 5, wherein the extractive reagent further comprises ethylene glycol, propylene glycol, glycol analogs or mixtures thereof.

9. The test sample extract of claim 5, wherein the divalent metal salt is selected from the group consisting of zinc sulfate, zinc acetate, zinc nitrate, zinc chloride, and mixtures of two or more of these metal salts.

10. The test sample extract of claim 5, wherein the divalent metal salt of zinc comprises zinc sulfate.

11. An extractive reagent composition comprising dimethyl sulfoxide, a glycol, at least one divalent metal salt of zinc and water, wherein the dimethyl sulfoxide is at least about 50% by volume of the extractive reagent composition, the glycol is about 30%-33% by volume of the extractive reagent composition, and the divalent metal salt of zinc is at a concentration of about 5 mM to about 400 mM in the extractive reagent composition, wherein the glycol is selected from the group consisting of ethylene glycol, propylene glycol, glycol analogs and mixtures thereof.

12. A kit comprising:
(a) at least one antibody that binds specifically to sirolimus;
(b) an extractive reagent composition comprising dimethyl sulfoxide, a glycol, and at least one divalent metal salt of zinc and water, wherein the dimethyl sulfoxide is at least about 50% of the extractive reagent composition, the divalent metal salt of zinc is at a concentration of about 30 mM to about 75 mM in the extractive reagent composition, and the glycol is selected from the group consisting of ethylene glycol, propylene glycol, glycol analogs or mixtures thereof; and
(c) a control composition comprising sirolimus or everolimus, wherein (a), (b) and (c) are provided in separate containers.

13. The kit of claim 12, wherein the divalent metal salt of zinc is selected from the group consisting of zinc sulfate, zinc acetate, zinc nitrate, zinc chloride, and mixtures of two or more of these metal salts.

\* \* \* \* \*